(12) United States Patent
Murakami et al.

(10) Patent No.: US 8,729,086 B2
(45) Date of Patent: May 20, 2014

(54) FIBROSIS INHIBITOR

(75) Inventors: Koji Murakami, Kyoto (JP); Takuya Toramoto, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 352 days.

(21) Appl. No.: 12/919,885

(22) PCT Filed: Feb. 26, 2009

(86) PCT No.: PCT/JP2009/053582
§ 371 (c)(1),
(2), (4) Date: Aug. 27, 2010

(87) PCT Pub. No.: WO2009/107736
PCT Pub. Date: Sep. 3, 2009

(65) Prior Publication Data
US 2011/0015211 A1 Jan. 20, 2011

(30) Foreign Application Priority Data
Feb. 28, 2008 (JP) ................................. 2008-046999

(51) Int. Cl.
*A61K 31/4965* (2006.01)
*C07D 241/02* (2006.01)

(52) U.S. Cl.
USPC .................... 514/255.06; 544/336

(58) Field of Classification Search
USPC .................... 514/255.06; 544/336
See application file for complete search history.

(56) References Cited

U.S. PATENT DOCUMENTS

| | | | |
|---|---|---|---|
| 6,046,233 A | 4/2000 | Kasukawa et al. | |
| 7,205,302 B2 * | 4/2007 | Asaki et al. | 514/252.1 |
| 2004/0102436 A1 | 5/2004 | Asaki et al. | |
| 2004/0116530 A1 * | 6/2004 | Maeda et al. | 514/573 |

FOREIGN PATENT DOCUMENTS

| | | |
|---|---|---|
| EP | 0759297 A1 | 2/1997 |
| EP | 1380307 A1 | 1/2004 |
| WO | 02/088084 A1 | 11/2002 |
| WO | 2006113704 A2 | 10/2006 |
| WO | 2010018549 A2 | 2/2010 |
| WO | 2010075861 A2 | 7/2010 |

OTHER PUBLICATIONS

Kuwano, K., et al. "2-{4-[5,6-Diphenylpyrazin-2-yl)(isopropyl)amino]butoxy}-N-(methylsulfonyl)acetamide (NS-304), an Orally Available and Long-Acting Prostacyclin Receptor Agonist Prodrug." The Journal of Pharmacology and Experimental Therapeutics. (2007), 322 (3), 1181-1188.*

Liu, X., et al. "Fibrotic lung fibroblasts show blunted inhibition by cAMP due to deficient CREB phosphorylation." American Society for Pharmacology and Experimental Therapeutics. Aug. 3, 2005.*
Kuwano, K., et al. "2-{4-[(5,6-Diphenylpyrazin-2-yl)(isopropyl)amino]butoxy}-N-(methylsulfonyl)acetamide (NS-304), an Orally Available and Long-Acting Prostacyclin Receptor Agonist Prodrug." Journal of Pharmacology and Experimental Therapeutics. (2007), vol. 322, No. 3, pp. 1181-1188.*
PCT International Preliminary Report on Patentability for PCT/JP2009/053582 issued on Oct. 12, 2010.
Shinsuke Murakami, "Investigation of therapeutic effect on pulmonary fibrosis of a long-acting PGI2 agonist (ONO-1301) which simultaneously has an inhibitory effect on TXA synthetase," The Journal of the Japanese Respiratory Society, 2005, vol. 43, pp. 253.
Shinsuke Murakami et al., Prostacyclin agonist with thromboxane synthase inhibitory activity (ONO-1301) attenuates bleomycin-induced pulmonary fibrosis in mice, Am J Physiol Lung Cell Mol Physiol 290: 59-65, 2006. First published Sep. 9, 2005.
A. Nakamura et al., Synthesis and evaluation of N-acylsulfonamide and N-acylsulfonylurea prodrugs of a prostacyclin receptor agonist, Bioorganic & Medicinal Chemistry, vol. 15, 2007, pp. 7720-7725.
An Extended European Search Report, dated Nov. 23, 2011, which issued during the prosecution of European Application No. 09714302.8, which corresponds to the present application.

* cited by examiner

*Primary Examiner* — Andrew D Kosar
*Assistant Examiner* — John S Kenyon
(74) *Attorney, Agent, or Firm* — McDermott Will & Emery LLP

(57) ABSTRACT

[Object] The main object of the present invention is to provide a fibrosis inhibitor.
[Solving Means] The present invention relates to a fibrosis inhibitor containing the heterocyclic derivative represented by the following general formula (1) or a pharmaceutically acceptable salt thereof as an active ingredient;

[chem. 1]

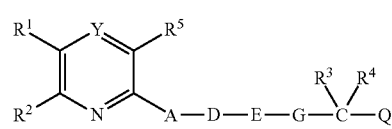

(1)

In the formula (1),
$R^1$ and $R^2$ are the same or different and each represents an optionally substituted aryl;
$R^3$ and $R^4$ are the same or different and each represents hydrogen atom or alkyl;
$R^5$ represents hydrogen atom, alkyl or halogen atom;
Y represents N or N→O;
A represents $NR^6$, and $R^6$ represents hydrogen atom, alkyl, etc.;
D represents alkylene or alkenylene which is optionally substituted with hydroxy;
E represents phenylene or a single bond;
G represents O, S, etc.; and
Q represents carboxy, alkoxycarbonyl, etc.

1 Claim, 5 Drawing Sheets

\#: p < 0.05 vs non-stimulated control by t-test (n = 5)

\*\*: p < 0.01 vs control by Dunnett's test (n = 5)

\#\#: p < 0.01 vs non-stimulated control by t-test (n = 3)

\*\*: p < 0.01 vs control by t-test (n = 3)

\##: p < 0.01 vs non-stimulated control by t-test (n = 4)

\*: p < 0.05 vs control by Dunnett's test

\*\*: p < 0.01 vs control by Dunnett's test (n = 4)

: p < 0.01 vs non-stimulated control by t-test (n = 3)

**: p < 0.01 vs control by Dunnett's test (n = 3)

\#: $p < 0.05$ vs non-stimulated control by t-test (n = 2)

*: $p < 0.05$ vs control by Dunnett's test

**: $p < 0.01$ vs control by Dunnett's test (n = 2)

FIBROSIS INHIBITOR

CROSS REFERENCE TO PRIOR APPLICATIONS

This application is a U.S. National Phase application under 35 U.S.C. §371 of International Application No. PCT/JP2009/053582, filed on Feb. 26, 2009 and claims benefit of priority to Japanese Patent Application No. 2008-046999, filed on Feb. 28, 2008. The International Application was published in Japanese on Sep. 3, 2009 as WO 2009/107736 A1 under PCT Article 21(2). The contents of these applications are hereby incorporated by reference.

TECHNICAL FIELD

The present invention relates to a fibrosis inhibitor containing a heterocyclic derivative (hereinafter, referred to as "the present heterocyclic derivative (1)") represented by the following general formula (1) or a pharmaceutically acceptable salt thereof as an active ingredient;

[Formula 1]

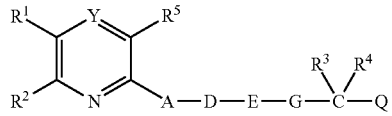

(1)

In the formula (1), $R^1$ and $R^2$ are the same or different and each represents an optionally substituted aryl, wherein the substitutions are the same or different and one to three substitutions are selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

$R^3$ and $R^4$ are the same or different and each represents hydrogen atom or alkyl;

$R^5$ represents hydrogen atom, alkyl or halogen atom;

Y represents N or N→O;

A represents $NR^6$, and $R^6$ represents hydrogen atom, alkyl, alkenyl or cycloalkyl;

D represents alkylene or alkenylene which is optionally substituted with hydroxy, or A and D are combined with each other to form a divalent group represented by the following formula (2)

[Formula 2]

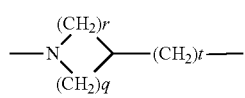

(2)

Wherein, r represents an integer of 0 to 2, q represents 2 or 3 and t represents an integer of 0 to 4;

E represents phenylene or a single bond, or D and E are combined with each other to form a divalent group represented by the following formula (3)

[Formula 3]

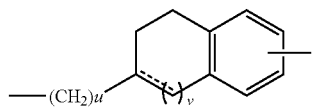

(3)

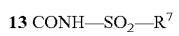 represents a single bond or a double bond;
u represents an integer of 0 to 2 and v represents 0 or 1;
G represents O, S, SO or $SO_2$; and
Q represents carboxy, alkoxycarbonyl, tetrazolyl, carbamoyl, monoalkylcarbamoyl, dialkylcarbamoyl or the group represented by the following formula (4).

[Formula 4]

$$13\ CONH-SO_2-R^7 \quad (4)$$

Wherein, $R^7$ represents amino, monoalkylamino, dialkylamino, hydroxy, any of the group of the following 1) to 4) which are optionally substituted with 1 to 3 substituents selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;
1) alkyl,
2) aryl,
3) aryloxy, and
4) heterocyclic group.

BACKGROUND ART

Fibrosis of organs occurs in such a manner that extracellular matrix is excessively accumulated in the organs through invasion or injury of organs due to some cause. When the degree of damage of organs due to invasion or injury is slight, cicatrix does not remain and the organs return to normal. However, when the degree of damage of the organs due to invasion or injury is severe or sustained, fibrosis of the cicatrix gives impairment of its inherent function. Further, it induces new fibrosis and generates a vicious cycle of fibrosis, finally, dysfunction of organs occurs.

As a disease caused by fibrosis of organs, interstitial pneumonia (pulmonary fibrosis), etc. have been known. Interstitial pneumonia is a disease where inflammation happens in alveolar wall due to some causes; fibroblasts proliferate in interstitial tissues; the lung is sclerosed by an excessive sedimentation of collagen fibers; gas exchange is disturbed; and, finally, respiratory failure occurs. After onset of the disease, the patient dies within three to five years in average. The detailed mechanism of pathogenesis of interstitial pneumonia has not been clarified yet and no established treating method has been available yet as well.

It has recently been reported that, in interstitial pneumonia model mice induced by bleomycin, ONO-1301 which is a prostaglandin $I_2$ (hereinafter, referred to as "$PGI_2$") receptor agonist has a inhibitive effect for interstitial pneumonia (see, for example, Non-Patent Document 1).

The present heterocyclic derivative (1) or a pharmaceutically acceptable salt thereof has already been reported to be useful for the treatment of pulmonary hypertension and obstructive arteriosclerosis as a $PGI_2$ receptor agonist (see, for example, Patent Document 1).

Patent Document 1: Pamphlet of International Publication WO 02/088084

Non-Patent Document 1: Am J Physiol Lung Cell Mol Physiol 290: L59-L65, 2006

DISCLOSURE OF THE INVENTION

Problems that the Invention is to Solve

The main object of the present invention is to provide a novel fibrosis inhibitor.

Means for Solving the Problems

The present inventors have found that the present heterocyclic derivative (1) has an inhibitory effect of the growth of fibroblasts and have achieved the present invention.

An example of the present invention is a fibrosis inhibitor containing the present heterocyclic derivative (1) or a pharmaceutically acceptable salt thereof as an active ingredient.

BEST MODE FOR CARRYING OUT THE INVENTION

In the present heterocyclic derivative (1), the preferred one is that where $R^1$ and $R^2$ are the same or different and each represents optionally substituted phenyl, and the substitutions are the same or different and one to three substitutions are selected from the group consisting of halogen atom, alkyl and alkoxy;

$R^3$ and $R^4$ are the same or different and each represents hydrogen atom or alkyl;

$R^5$ represents hydrogen atom;

Y represents N;

A represents $NR^6$, and $R^6$ represents alkyl;

D represents alkylene;

E represents a single bond;

G represents O; and

Q represents carboxy or a group represented by the following formula (4), and $R^7$ represents amino, monoalkylamino, dialkylamino, hydroxy, or any of the group of the following 1) to 4) which are optionally substituted with 1 to 3 substituents selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

1) alkyl,
2) aryl,
3) aryloxy, and
4) heterocyclic group.

To be more specific, 2-{4-[N-(5,6-diphenylpyrazin-2-yl)-N-isopropylamino]butyloxy}acetic acid (hereinafter, referred to as "the compound A") and 2-{4-[N-(5,6-diphenylpyrazin-2-yl)-N-isopropylamino]butyl-oxy}-N-(methylsulfonyl)acetamide (hereinafter, referred to as "the compound B") are preferable for example.

As to the "alkyl" in the present invention, that which is straight or branched having 1 to 6 carbon atoms, for example, methyl, ethyl, n-propyl, isopropyl, n-butyl, isobutyl, sec-butyl, tert-butyl, n-pentyl, isopentyl, n-hexyl or isohexyl may be exemplified. Particularly, alkyl having 1 to 4 carbon atoms is preferable.

As to an alkyl moiety in "haloalkyl", "arylalkyl", "alkylthio", "alkoxyalkyl", "alkylsulfonyl", "monoalkylamino", "dialkylamino", "monoalkylcarbazoyl" and "dialkylcarbamoyl" in the present invention, that which is the same as the already-mentioned alkyl may be exemplified.

As to the "alkoxy" in the present invention, that which is straight or branched having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy or isohexyloxy may be exemplified. Particularly, alkoxy having 1 to 4 carbon atoms is preferable.

As to an alkoxy moiety in "alkoxycarbonyl" and "alkoxyalkyl" in the present invention, that which is the same as the already-mentioned alkoxy may be exemplified.

As to the "alkenyl" in the present invention, that which is straight or branched having 2 to 6 carbon atoms, for example, vinyl, 1-propenyl, 2-propenyl, 1-butenyl, 2-butenyl, 3-butenyl, 1-pentenyl, 2-pentenyl, 3-pentenyl, 4-pentenyl, 4-methyl-3-pentenyl, 1-hexenyl, 2-hexenyl, 3-hexenyl, 4-henexyl or 5-hexenyl may be exemplified. Particularly, alkenyl having 3 or 4 carbon atoms is preferable.

As to the "cycloalkyl" in the present invention, that which has 3 to 8 carbon atoms, for example, cyclopropyl, cyclobutyl, cyclopentyl, cyclohexyl, cycloheptyl or cyclooctyl may be exemplified. Particularly, cycloalkyo having 5 to 7 carbon atoms is preferable.

As to the "halogen atom" in the present invention, fluorine atom, chlorine atom, bromine atom and iodine atom may be exemplified.

As to the "aryl" in the present invention, that which has 6 to 10 carbon atoms, for example, phenyl, 1-naphthyl or 2-naphthyl may be exemplified. Particularly, phenyl is preferable.

As to the aryl moiety in "arylalkyl" and "aryloxy" in the present invention, that which is the same as in the already-mentioned aryl may be exemplified.

As to the "alkylene" in the present invention, that which is straight or branched having 1 to 8 carbon atoms, for example, methylene, ethylene, 1-methylethylene, 2-methylethylene, trimethylene, tetramethylene, pentamethylene, hexamethylene, heptamethylene or octamethylene may be exemplified. Particularly, alkylene having 3 to 6 carbon atoms is preferable, and alkylene having 4 carbon atoms is more preferable.

As to the "alkenylene" in the present invention, that which is straight or branched having 2 to 8 carbon atoms, for example, ethenylene, 1-propenylene, 2-propenylene, 1-butenylene, 2-butenylene, 3-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene, 5-hexenylene, 1-heptenylene, 2-heptenylene, 3-heptenylene, 4-heptenylene, 5-heptenylene, 6-heptenylene, 1-octenylene, 2-octenylene, 3-octenylene, 4-octenylene, 5-octenylene, 6-octenylene or 7-octenylene may be exemplified. Particularly, alkenylene having 3 to 6 carbon atoms is preferable, and alkenylene having 4 carbon atoms is more preferable.

As to the "heterocyclic group" in the present invention, the following (1) or (2) may be exemplified.

(1) A five- to six-membered aromatic ring group having 1 to 4 hetero atoms selected from nitrogen atom, oxygen atom and sulfur atom, or a benzene condensed ring thereof and nitrogen atom and sulfur atom may form an oxide when a ring-constituent atom is nitrogen atom or sulfur atom. Examples thereof include 1-pyrrolyl, 2-pyrrolyl, 3-pyrrolyl, 3-indolyl, 2-furanyl, 3-furanyl, 3-benzofuranyl, 2-thienyl, 3-thienyl, 3-benzothienyl, 1,3-oxazol-2-yl, 4-isoxazolyl, 2-thiazolyl, 5-thiazolyl, 2-benzothiazolyl, 1-imidazolyl, 2-imidazolyl, 4-imidazolyl, 2-benzimidaolyl, 1H-1,2,4-triazol-1-yl, 1H-tetrazol-5-yl, 2H-tetrazol-5-yl, 2-pyridyl, 3-pyridyl, 4-pyridyl, 3-pyrazolyl, 2-pyrimidinyl 4-pyrimidinyl, 2-pyrazinyl, and 1,3,5-triazin-2-yl.

(2) A four- to eight-membered saturated ring group which optionally has one to four same or different nitrogen atom, oxygen atom or sulfur atom, or a benzene condensed ring thereof, and nitrogen atom and sulfur atom may form an oxide when a ring-constituent atom is nitrogen atom or sulfur atom. Examples thereof include piperidino, piperazinyl, 3-methylpiperazin-1-yl, homopiperazinyl, morpholino, thiomorpholino, 1-pyrrolidinyl, 2-pyrrolidinyl and 2-tetrahydrofuranyl.

The present heterocyclic derivative (1) is able to be synthesized by the process mentioned in the above-mentioned Patent Document 1 (pamphlet of International Publication WO 02/088084).

Although the present heterocyclic derivative (1) may be used as a pharmaceutical just in a form of free base or acid, it is also possible to use by making into a form of a pharmaceutically acceptable salt by a known method.

Examples of the "salt" when the present heterocyclic derivative (1) shows basicity include a salt with inorganic acid such as hydrochloric acid, sulfuric acid, nitric acid, phosphoric acid, hydrofluoric acid or hydrobromic acid and with organic acid such as acetic acid, tartaric acid, lactic acid, citric acid, fumaric acid, maleic acid, succinic acid, methanesulfonic acid, ethanesulfonic acid, benzenesulfonic acid, p-toluenesulfonic acid, naphthalenesulfonic acid or camphorsulfonic acid.

Examples of the "salt" when the present heterocyclic derivative (1) shows acidity include alkali metal salt such as sodium salt or potassium salt and alkali earth metal salt such as calcium salt.

There are geometrical isomers (Z and E substances) in the present heterocyclic derivative (1) and each of the geometrical isomers and a mixture thereof are also included in the present heterocyclic derivative (1). Some of the present heterocyclic derivative (1) has asymmetric carbon(s) and each of optical isomers and racemic substance thereof are also included in the present heterocyclic derivative (1). An optical isomer is able to be produced by subjecting the racemic substance prepared as above to an optical resolution by a known method using an optically active acid (such as tartaric acid, benzoyltartaric acid, mandelic acid or 10-camphorsulfonic acid) utilizing the basicity or by using a previously-prepared optically active compound as a material.

The fibrosis inhibitor of the present invention is able to be used for the treatment of the following diseases, for example, in which fibrosis of organs or tissues is involved.

(1) Renal Diseases
Tubulointerstitial nephritis
(2) Respiratory Diseases
Interstitial pneumonia (pulmonary fibrosis)
(3) Gastrointestinal Diseases
Hepatocirrhosis, chronic pancreatitis and scirrhous gastric cancer
(4) Cardiovascular Diseases
Myocardial fibrosis
(5) Bone and Articular Diseases
Bone marrow fibrosis and rheumatoid arthritis
(6) Skin Diseases
Postsurgical scar, burn scar, keloid, hypertrophic scar and scleroderma
(7) Obstetric Diseases
Hysteromyoma
(8) Urologic Diseases
Prostatic hypertrophy
(9) Other Diseases
Alzheimer's disease, sclerosing peritonitis, type I diabetes and post surgical adhesion The fibrosis inhibitor of the present invention is the present heterocyclic derivative (1) as it is or contains it in a pharmaceutically acceptable, nontoxic and inert carrier at a rate ranging from 0.01 to 99.5% or, preferably, ranging from 0.5 to 90%.

Examples of the carrier include solid, semi-solid or liquid diluent, filler and other auxiliary agents for pharmaceutical formulation. These can be used alone or as a mixture of two or more thereof.

The fibrosis inhibitor of the present invention may be in any of the forms of oral preparations such as powder, capsules, tablets, sugar-coated tablets, granules, diluted powder, suspension, liquid, syrup, elixir or troche and parenteral preparations such as injection or suppository in a solid or liquid dose unit. It may also be in a form of a sustained release preparation. Among them, oral preparations such as tablets are particularly preferable.

Powder is able to be manufactured by making the present heterocyclic derivative (1) into an appropriate fine size.

Diluted powder is able to be manufactured by such a manner that the present heterocyclic derivative (1) is made into an appropriate fine size and then mixed with a pharmaceutical carrier which is similarly made into the fine size such as edible carbohydrate (e.g., starch and mannitol). Flavoring agent, preservative, dispersing agent, coloring agent, perfume, etc. may be optionally added thereto.

Capsules are able to be manufactured by such a manner that the powder or diluted powder which is made powdery as mentioned above or granules which will be mentioned under the item for tablets is/are filled in an capsule shell such as gelatin capsule. It is also possible to manufacture in such a manner that the powdery thing is mixed with a lubricant or a fluidizing agent such as colloidal silica, talc, magnesium stearate, calcium stearate or solid polyethylene glycol followed by subjecting to a filling operation. When a disintegrating agent or solubilizing agent such as carboxymethyl cellulose, carboxymethyl cellulose calcium, lowly-substituted hydroxypropyl cellulose, croscarmellose sodium, carboxymethyl starch sodium, calcium carbonate or sodium carbonate is added, efficacy of the pharmaceutical when the capsules are ingested is able to be improved. It is also possible that fine powder of the present heterocyclic derivative (1) is suspended/dispersed in vegetable oil, polyethylene glycol, glycerol or surfactant and wrapped with a gelatin sheet to give a soft capsule preparation.

Tablets are able to be manufactured in such a manner that a powdery mixture is prepared by addition of a filler and made into granules or slugs and then a disintegrating agent or a lubricant is added thereto followed by making into tablets.

The powdery mixture is able to be manufactured by mixing an appropriately powdered substance with the above diluent or base. If necessary, it is possible to add a binder (such as carboxymethyl cellulose sodium, methyl cellulose, hydroxypropyl methyl cellulose, gelatin, polyvinylpyrrolidone or polyvinyl alcohol), a dissolution retarding agent (such as paraffin), a reabsorbing agent (such as a quaternary salt), an adsorbent (such as bentonite or kaolin), etc. thereto.

The powdery mixture is able to be made into granules in such a manner that it is firstly made wet using, for example, syrup, starch paste, acacia, cellulose solution or polymer solution, mixed with stirring and dried followed by grinding. Instead of making the powder into granules as such, it is also possible that the powder is applied to a tabletting machine and the resulting slug in an incomplete shape is ground to give granules. When a lubricant such as stearic acid, stearate, talc or mineral oil is added to the granules prepared as such, sticking of the granules each other is able to be prevented.

Tablets are also able to be manufactured in such a manner that the present heterocyclic derivative (1) is mixed with a fluid inert carrier and then directly making into tablets without conducting the above steps of making into granules or slugs.

The tablets prepared as such are able to be subjected to film coating or sugar coating. It is also possible to apply a transparent or semi-transparent protective coat comprising a tightly closed shellac film, a coat comprising sugar or polymer material or a polished coat comprising wax.

In other oral preparation such as liquid, syrup, troche or elixir, it is also possible to make into a dose unit form where a predetermined amount thereof contains a predetermined amount of the present heterocyclic derivative (1).

The syrup is able to be manufactured by dissolving the present heterocyclic derivative (1) into an appropriate aqueous solution of flavor. The elixir is able to be manufactured using a non-toxic alcoholic carrier.

The suspension is able to be manufactured by dispersing the present heterocyclic derivative (1) into a non-toxic carrier. If necessary, it is possible to add a solubilizing agent or an emulsifier (such as ethoxylated isostearyl alcohol or polyoxyethylene sorbitol ester), a preservative or a flavor-endowing agent (such as peppermint oil or saccharine) thereto.

If necessary, the dose unit formulation for oral administration may be made into microcapsules. The above formulation is also able to be coated or embedded into polymer or wax to obtain a prolonged action or sustained release of the active ingredient.

The parenteral preparation is able to be in a liquid dose unit form for subcutaneous, intramuscular or intravenous injection such as in a form of solution or suspension. The parenteral preparation is able to be manufactured in such a manner that a predetermined amount of the present heterocyclic derivative (1) is suspended or dissolved into a non-toxic liquid carrier meeting the purpose of injection such as aqueous or oily medium and then the suspension or solution is sterilized. Non-toxic salt or a solution thereof may be added thereto for making the injection solution isotonic. It is also possible to add a stabilizer, a preservative, an emulsifier and the like.

The suppository is able to be manufactured by dissolving or suspending the present heterocyclic derivative (1) into a low-melting and water-soluble or insoluble solid such as polyethylene glycol, cacao fat, semi-synthetic fat/oil (such as Witepsol (registered trade mark)), higher ester (such as myristyl palmitate) or a mixture thereof.

Although the dose of the fibrosis inhibitor of the present invention may vary depending upon the state of a patient such as body weight or age, administering route or degree of symptom, a range of 0.01 mg to 1000 mg/day as an amount of the present heterocyclic derivative (1) is generally suitable for an adult and a range of 0.1 mg to 100 mg is more preferable. In some cases, the dose less than the above may be sufficient or, on the other hand, the dose more than the above may be necessary. It is also possible to administer one to several times a day or to administer with an interval of one to several days.

EXAMPLES

The present invention will now be illustrated in more detail by way of the following test examples although the present invention is not limited to the scope mentioned in the examples.

Test Example 1

(1) Methods

Human Lung fibroblasts (manufactured by Lonza Walkersville; hereinafter, the same product will be used) were cultured in growth medium, which consisted of basal medium for human lung fibroblasts (manufactured by Lonza Walkersville; hereinafter, the same product will be used and referred to as "basal medium") with FGM-2 additional factor set (manufactured by Lonza Walkersville; hereinafter, the same product will be used) under the condition of 37° C. and 5% $CO_2$. The human lung fibroblasts were seeded in 96-well plate at $1\times10^3$ cell/well and incubated overnight in growth medium.

The fibroblasts were washed once with 100 μL of phosphate-buffered saline (manufactured by Nissui Seiyaku; hereinafter, the same product will be used) and 100 μL of basal medium was added thereto followed by incubation for 24 hours. They were further washed with 100 μL of phosphate-buffered saline once and then basal medium was added in an amount of 80 μL/well. Ten μL of a 100 μM solution of the compound A or the compound B was added to each well and incubated for 2 hours. The solution added thereto was prepared in such a manner that the compound A or B was previously dissolved in dimethyl sulfoxide (DMSO) and the resulting 10 mM solution was diluted 100-fold with basal medium. For the non-stimulated control group and the control group, DMSO which was diluted 100-fold with basal medium was used.

Then a 100 ng/mL solution of epidermal growth factor (EGF) (manufactured by Pepro Tech) was added in an amount of 10 μL to each well and incubated for 48 hours. For a non-stimulated control group, the basal medium was used.

After incubating for 48 hours, absorbance at 490 nm was measured using Cell Titer 96, AQueous Assay (manufactured by Promega) for the analysis of cell proliferation activity. For the measurement of the absorbance, a microplate reader (Benchmark, manufactured by Bio-Rad; hereinafter, the same one will be used) was used.

(2) Results

As shown in FIG. 1, cell proliferation activity of the human lung fibroblasts significantly increased by stimulation with EGF. On the contrary, in the cells treated with the compounds A or B, the cell proliferation activity significantly decreased as compared with the control group.

Test Example 2

(1) Methods

Human lung fibroblasts were incubated in growth medium under the condition of 37° C. and 5% $CO_2$. The human lung fibroblasts were seeded in 96-well plate at $3\times10^3$ cell/well and incubated overnight in growth medium.

The fibroblasts were washed once with 100 μL of phosphate-buffered saline. Then basal medium was added thereto and incubation was conducted for 24 hours. They were further washed with 100 μL of phosphate-buffered saline once and then basal medium was added in an amount of 80 μL/well. Ten μL of a 1 μM solution of the compound A was added to each well and incubated for 2 hours. The solution used therefor was prepared in such a manner that the compound A was previously dissolved in DMSO and the resulting 1 mM solution was diluted 100-fold with basal medium. For the non-stimulated control group and the control group, DMSO which was diluted 100-fold with the basal medium was used.

Then a 100 ng/mL solution of transforming growth factor-α(TGF-α) (manufactured by Chemicon) was added in an amount of 10 μL to each well and incubated for 48 hours. For a non-stimulated control group, the basal medium was used.

After incubating for 48 hours, absorbance at 490 nm was measured, in the same way as in Test Example 1, using a reagent for the analysis of cell proliferation activity. For the measurement of the absorbance, a microplate reader was used.

(2) Results

As shown in FIG. 2, cell proliferation activity of the human lung fibroblasts significantly increased by stimulation with TGF-α. On the contrary, in the cells treated with the compound A, the cell proliferation activity significantly decreased as compared with that of the control group.

Test Example 3

(1) Methods

Human lung fibroblasts were seeded in 96-well plate at $5 \times 10^3$ cells/well and incubated in the growth medium in the same way as in Test Example 1 overnight. The fibroblasts were washed once with 100 μL of basal medium and 100 μL of basal medium was added thereto followed by incubating for 24 hours. They were further washed once with 100 μL of basal medium and then 80 μL/well of basal medium was added. A 0.1, 1, 10 or 100 μl solution of the compound A was added in an amount of 10 μL to each well. The solution used therefor was prepared in such a manner that the compound A was previously dissolved in DMSO and adjusted to a concentration of 10 μM, 100 μM, 1 mM or 10 mM, followed by a 100-fold dilution with the basal medium. For the non-stimulated control group and the control group, DMSO which was diluted 100-fold with basal medium was added in an amount of 10 μL. After incubating for 2 hours, 10 μL of 100 ng/mL transforming growth factor β1 (TGFβ1) (manufactured by Pepro Tech; hereinafter, the same product will be used) was added and, for the non-stimulated control group, 10 μL of basal medium was added. After incubating for 48 hours, the medium was recovered for measuring the concentration of the type I pro-collagen C terminal peptide (PIP) in the medium, and after an addition of 100 μL of the basal medium, the cell proliferation activity was measured using 3-(4,5-dimethyl-2-thiazolyl)-2,5-diphenyl-2H-tetrazolium bromide (MTT) (manufactured by Nacalai Tesque). Measurement of the cell proliferation activity was conducted in such a manner that 10 μL of a 5 mg/mL MTT stock solution was added to each well, and after incubation for 4 hours, 100 μL of a 0.04M isopropanol solution of hydrochloric acid was added to each well, followed by the absorbance measurement at 595 nm (reference wavelength: 655 nm) using a microplate reader. The PIP concentration after incubation for 48 hours was measured using a type I pro-collagen C-peptide (PIP) EIA kit (manufactured by Takara; hereinafter, the same one will be used) in accordance with the manual attached thereto. The evaluation of this test was carried out using the value (index for collagen production) calculated as a relative value where a mean value of the non-stimulated control group was defined as 1 after correcting the measured value of PIP concentration for the cell proliferation activity value (absorbance).

(2) Results

As shown in FIG. 3, production of collagen significantly increased in the human lung fibroblasts by stimulation with TGF β1. On the contrary, in the cells treated with the compound A, the collagen production significantly decreased as compared with that of the control group.

Test Example 4

(1) Methods

Human lung fibroblasts were seeded in 24-well plate at $1 \times 10^5$ cells/well and incubated in growth medium in the same way as in Test Example 1 overnight. The fibroblasts were washed once with 500 μL of basal medium, and added with 500 μL of basal medium followed by incubation for 24 hours. They were further washed once with 500 μL of basal medium and then 400 μL/well of basal medium was added. A 1, 10 or 100 μM solution of the compound A prepared by the same manner as in Test Example 3 was added in an amount of 50 μL to each well. For the non-stimulated control group and the control group, DMSO which was diluted 100-fold with basal medium was added in an amount of 50 μL. After incubating for 2 hours, 50 μL of a 100 ng/mL TGF β1 solution was added to each well and, for the non-stimulated control group, 50 μL of basal medium was added. After incubating for 24 hours, RNA was extracted using an SV Total RNA Isolation System (manufactured by Invitrogen) and the 1st strand cDNA was synthesized from the RNA using a Superscript III (manufactured by Invitrogen). Using the cDNA prepared as above as a template, expressed amount of mRNA for type I collagen α1 chain (COL 1α1), type I collagen α2 chain (COL 1α2), α smooth muscle actin (ACTA), TGF β1 and glyceraldehydes 3-phosphate dehydrogenase (GAPDH) were measured by means of a real-time quantitative PCR method. The real-time quantitative PCR was conducted using Platinum SYBR Green qPCR Super-Mix-UDG with ROX (manufactured by Invitrogen) and a primer being specific to each gene in accordance with the manual attached to the Platinum SYBR Green qPCR Super-Mix-UDG with ROX using ABI PRISM 7000 (Applied Biosystems). The evaluation of this test was carried out using the value (mRNA expression level) calculated as a relative value where a mean value of the non-stimulated control group was defined as 1 after correcting the expressed value of mRNA of each gene for the expressed amount of mRMA of GAPDH.

(2) Results

As shown in FIGS. 4 to 7, in the human lung fibroblasts, each mRNA expression level increased by stimulation with TGF μ1. On the contrary, in the cells treated with the compound A, each mRNA level decreased as compared with that of the control group.

Test Example 5

(1) Methods

Rat renal interstitial cells (NRF 49F cells) were seeded in 96-well plate at $1 \times 10^4$ cells/well and incubated in an Minimum Essential Medium (MEM medium; manufactured by Nippon Seiyaku; hereinafter, the same product will be used) containing 10% of bovine fetal serum (manufactured by JRH Bioscience; hereinafter, the same product will be used) under the condition of 37° C. and 5% $CO_2$ overnight. The cells were washed once with an MEM medium containing no bovine fetal serum (hereinafter, referred to as "serum-free MEM medium"), and 100 μL of the serum-free MEM medium was added thereto followed by incubation for 24 hours. After washing with serum-free MEM medium once, serum-free MEM medium was added in an amount of 80 μL/well. A 100 μM solution of the compound A prepared by the same method as in Test Example 1 was added in an amount of 10 μL to each well. For the non-stimulated control group and the control group, DMSO which was diluted 100-fold with serum-free MEM medium was added in an amount of 10 μL. After incubating for 2 hours, 10 μL of a 100 ng/mL platelet-derived growth factor BB (PDGF BB; manufactured by Sigma) solution was added to each well and, for the non-stimulated control group, 10 μL of serum-free MEM medium was added followed by incubating. After incubating for 48 hours, cell proliferation activity (absorbance) was measured by an MTT method in the same way as in Test Example 3. The evaluation of this test was carried out using the value (cell proliferation level) expressed as a relative value where a mean value of absorption of the non-stimulating control group was defined as 1.

(2) Results

As shown in FIG. 8, in the rat renal interstitial cells, cell proliferation level significantly increased by stimulation with PDGF BB. On the contrary, in the cells treated with the compound A, the cell proliferation level significantly decreased as compared with that of the control group.

Test Example 6

(1) Methods

Human skin fibroblasts (manufactured by Kurabo; hereinafter, the same product will be used) were seeded in 96-well plate at $5 \times 10^3$ cells/well and incubated in a Dulbecco's modified Eagle's medium (DMEM medium; manufactured by Nippon Seiyaku; hereinafter, the same product will be used) containing 10% of bovine fetal serum under the condition of 37° C. and 5% $CO_2$ overnight. The human skin fibroblasts were washed once with an DMEM medium containing no bovine fetal serum (hereinafter, referred to as "serum-free DMEM medium"), and 100 μL of serum-free DMEM medium was added thereto followed by incubation for 24 hours. After washing with serum-free DMEM medium once more, serum-free DMEM medium was added in an amount of 80 μL/well. Ten μL of the 0.1, 1, 10 or 100 μM solution of the compound A prepared by the same method as in Test Example 3 was added to each well. For the non-stimulated control group and the control group, DMSO which was diluted 100-fold with serum-free DMEM medium was added in an amount of 10 μL each and followed by incubating. After incubating for 2 hours, 10 μL of a 100 ng/mL TGF β1 solution was added to each well and, for the non-stimulated control group, each 10 μL of serum-free MEM medium was added. After incubating for 48 hours, cell proliferation activity (absorbance) was measured by the MTT method, and PIP concentration in the medium was measured in the same way as in Test Example 3. The evaluation of this test was carried out using the value (index for production of collagen) calculated as a relative value where a mean value in the non-stimulated control group was defined as 1 after correcting the measured value of PIP concentration using the cell proliferation activity value (absorbance).

(2) Results

As shown in FIG. 9, in the human skin fibroblasts, production of collagen significantly increased by stimulation with TGF β1. On the contrary, in the cells treated with the compound A, production of collagen significantly decreased as compared with that of the control group.

Figure 1:
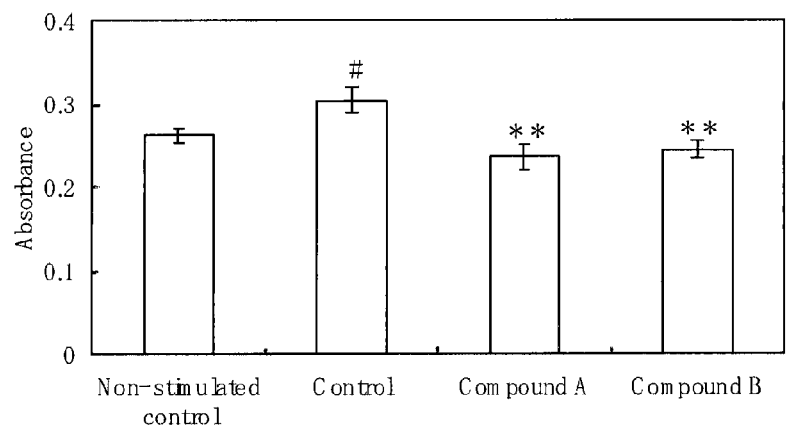
FIG. 1 shows the inhibitive effects of the compound A and the compound B on the proliferation of human lung fibroblasts stimulated by EGF. An ordinate shows absorbance.
Figure 2:
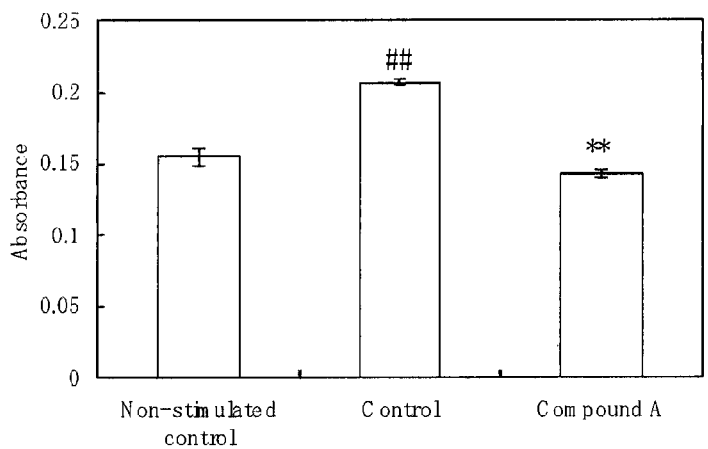
FIG. 2 shows the inhibitive effects of the compound A and the compound B on the proliferation of human lung fibroblasts stimulated by TGFα. An ordinate shows absorbance.
Figure 3:
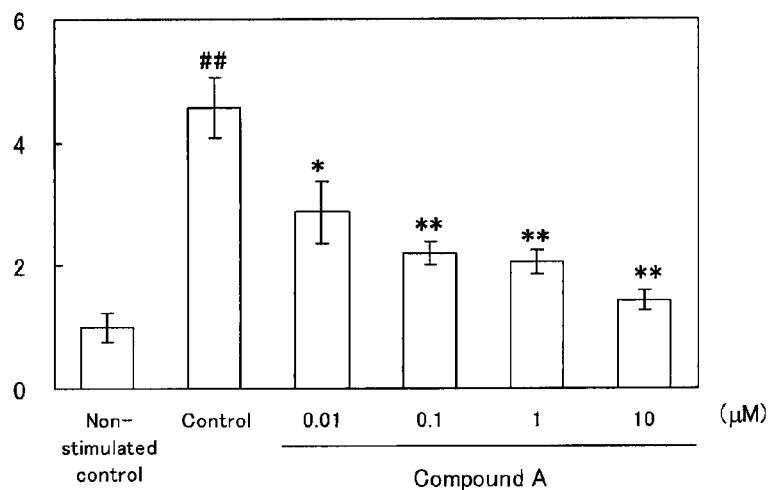
FIG. 3 shows the inhibitive effect of the compound A on the production of collagen in human lung fibroblasts stimulated by TGF β1. An ordinate shows the value calculated as a relative value where a mean value in the non-stimulated control group was defined as 1 after correcting the measured value for PIP concentration by the cell proliferation activity value (absorbance).
Figure 4:
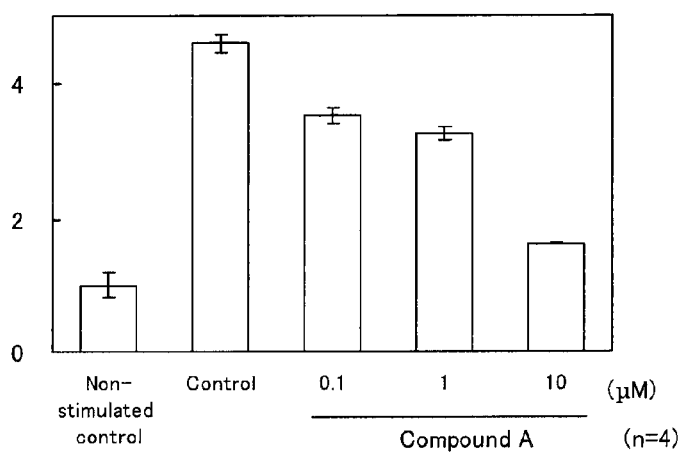
FIG. 4 shows the inhibitive effect of the compound A on COL 1α1 mRNA expression in human lung fibroblasts stimulated by TGF β1. An ordinate shows a relative value where a mean value in the non-stimulated control group was defined as 1 after correcting the expressed amount of mRNA by COL 1α1 using the expressed amount of mRNA by GAPDH.
Figure 5:
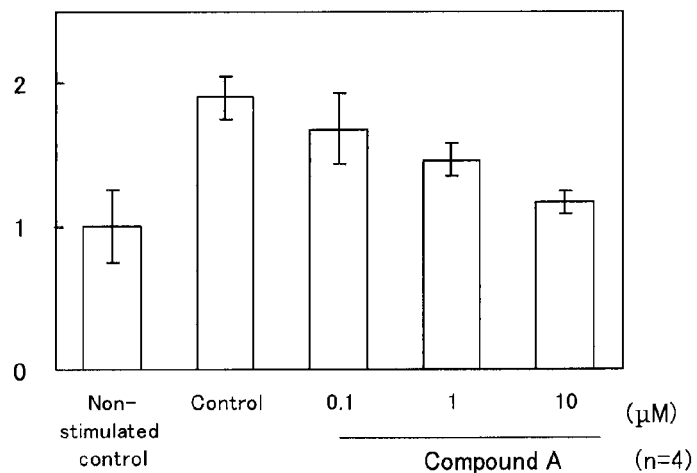
FIG. 5 shows the inhibitive effect of the compound A on COL 1α2 mRNA expression in human lung fibroblasts stimulated by TGF β1. An ordinate shows a relative value where a mean value in the non-stimulated control group was defined as 1 after correcting the expressed amount of mRNA by COL 1α2 using the expressed amount of mRNA by GAPDH.
Figure 6:
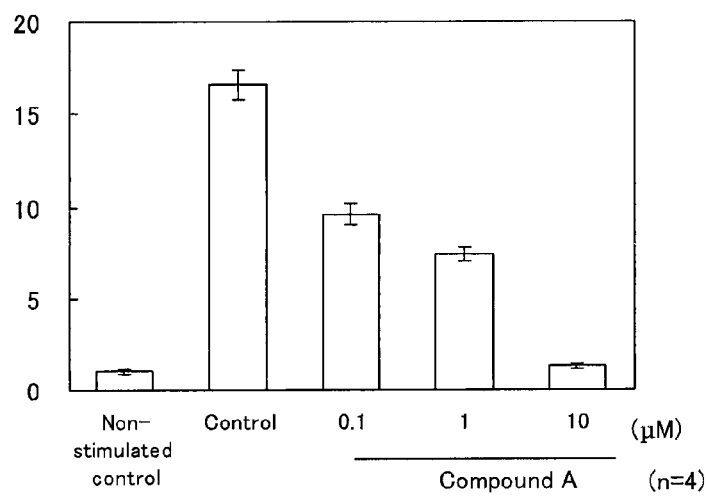
FIG. 6 shows the inhibitive effect of the compound A on ACTA mRNA expression in human lung fibroblasts stimulated by TGF β1. An ordinate shows a relative value where a mean value in the non-stimulated control group was defined as 1 after correcting the expressed amount of mRNA by ACTA using the expressed amount of mRNA by GAPDH.
Figure 7:
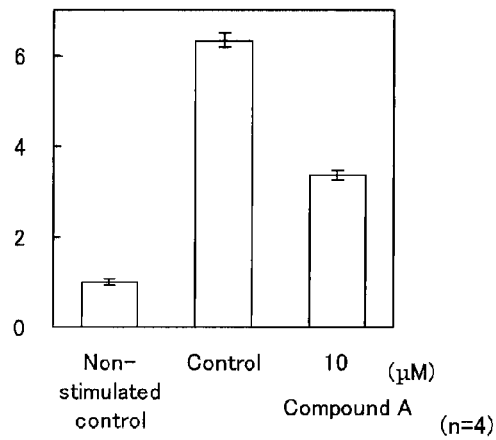
FIG. 7 shows the inhibitive effect of the compound A on TGF β1 mRNA expression in human lung fibroblasts stimulated by TGF β1. An ordinate shows a relative value where a mean value in the non-stimulated control group was defined as 1 after correcting the expressed amount of mRNA by TGF β1 using the expressed amount of mRNA by GAPDH.
Figure 8:
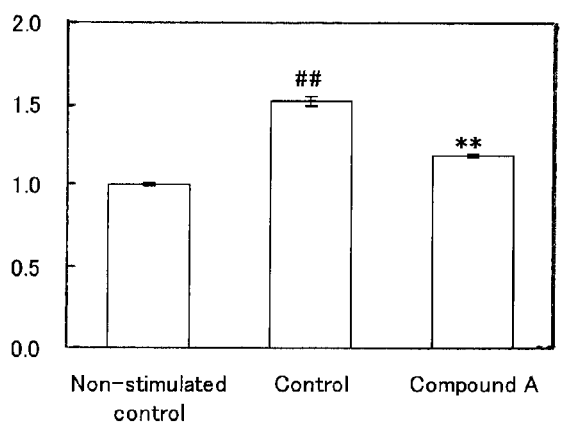
FIG. 8 shows the inhibitive effect of the compound A on the proliferation of rat renal interstitial cells stimulated by PDGF BB. An ordinate shows a relative value where a mean value of absorbance in the non-stimulated control group was defined as 1.
Figure 9:
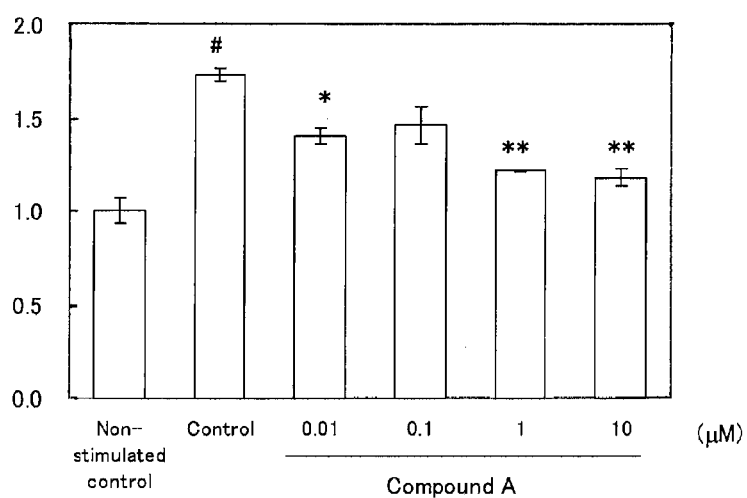
FIG. 9 shows the inhibitive effect of the compound A on the production of collagen in human skin fibroblasts stimulated by TGF β1. An ordinate shows a value calculated as a relative value where a mean value in the non-stimulated control group was defined as 1 after correcting the measured value of PIP concentration by the cell proliferation activity value (absorbance).

The invention claimed is:

1. A method for treating interstitial pneumonia comprising administering a fibrosis inhibitor containing 2-{4-[N-(5,6-diphenylpyrazin-2-yl)-N-isopropylamino]butyloxy}acetic acid, 2-{4[N-(5,6-diphenylpyrazin-2-yl)-N-isopropylamino]butyloxy}-N-(methylsulfonyl)acetamide or a pharmaceutically acceptable salt thereof as an active ingredient to a patient in need of such treatment.

* * * * *